(12) United States Patent
Avidor et al.

(10) Patent No.: US 8,523,777 B2
(45) Date of Patent: Sep. 3, 2013

(54) METHOD, APPARATUS AND SYSTEM FOR PREDICTING ELECTROMECHANICAL DISSOCIATION

(75) Inventors: Yoav Avidor, Tel-Aviv (IL); Hanan Keren, Kfar-Saba (IL)

(73) Assignee: Cheetah Medical, Inc., Wilmington, DE (US)

( * ) Notice: Subject to any disclaimer, the term of this patent is extended or adjusted under 35 U.S.C. 154(b) by 494 days.

(21) Appl. No.: 12/596,483

(22) PCT Filed: Apr. 15, 2008

(86) PCT No.: PCT/IL2008/000509
§ 371 (c)(1),
(2), (4) Date: Mar. 23, 2010

(87) PCT Pub. No.: WO2008/129535
PCT Pub. Date: Oct. 30, 2008

(65) Prior Publication Data
US 2010/0217140 A1 Aug. 26, 2010

Related U.S. Application Data

(63) Continuation-in-part of application No. 11/889,395, filed on Aug. 13, 2007.

(60) Provisional application No. 60/907,847, filed on Apr. 19, 2007.

(51) Int. Cl.
*A61B 8/06* (2006.01)

(52) U.S. Cl.
USPC ............ 600/454; 600/500; 600/506; 600/509

(58) Field of Classification Search
USPC ......................... 600/454, 509, 500
See application file for complete search history.

(56) References Cited

U.S. PATENT DOCUMENTS

| | | | |
|---|---|---|---|
| 3,340,867 A | 9/1967 | Kubicek et al. |
| 3,851,641 A | 12/1974 | Toole et al. |
| 3,874,368 A | 4/1975 | Asrican |
| 3,914,999 A | 10/1975 | Grandchamp |
| 4,094,309 A | 6/1978 | Grzenia |

(Continued)

FOREIGN PATENT DOCUMENTS

| | | |
|---|---|---|
| WO | WO 96/32883 | 10/1996 |
| WO | WO 97/11638 | 4/1997 |

(Continued)

OTHER PUBLICATIONS

Examiner's Report Dated Nov. 15, 2010 From the Australian Government, IP Australia Re. Application No. 2006215274.

(Continued)

*Primary Examiner* — Christopher D Koharski
*Assistant Examiner* — Natasha Patel

(57) ABSTRACT

A method of predicting onset of electromechanical dissociation in a heart of a subject is disclosed. The method comprises: extracting from the composite input signal an electrocardiac signal and determining electrical activity of the heart based on the electrocardiac signal; extracting from the composite input signal a radiofrequency signal and determining blood flow measure based on the radiofrequency signal; and if the blood flow measure is below a predetermined threshold and the electrical activity is above a predetermined threshold, then predicting the onset of electromechanical dissociation.

20 Claims, 9 Drawing Sheets

(56) References Cited

U.S. PATENT DOCUMENTS

| | | | |
|---|---|---|---|
| 4,153,048 A | 5/1979 | Magrini | |
| RE30,101 E | 9/1979 | Kubicek et al. | |
| 4,437,469 A | 3/1984 | Djordjevich et al. | |
| 4,450,527 A | 5/1984 | Sramek | |
| 4,537,200 A | 8/1985 | Widrow | |
| 4,610,254 A | 9/1986 | Morgan et al. | |
| 4,705,049 A | 11/1987 | John | |
| 4,781,201 A | 11/1988 | Wright et al. | |
| 4,803,431 A | 2/1989 | Sano et al. | |
| 4,805,621 A | 2/1989 | Heinze et al. | |
| 4,852,580 A | 8/1989 | Wood | |
| 4,870,578 A | 9/1989 | Vysin et al. | |
| 4,888,558 A | 12/1989 | Hereikson | |
| 4,926,868 A | 5/1990 | Larsen | |
| 4,953,556 A | 9/1990 | Evans | |
| 5,058,583 A | 10/1991 | Geddes et al. | |
| 5,158,093 A | 10/1992 | Shvartz et al. | |
| 5,178,154 A | 1/1993 | Ackmann et al. | |
| 5,309,917 A | 5/1994 | Wang et al. | |
| 5,316,004 A | 5/1994 | Chesney et al. | |
| 5,423,326 A | 6/1995 | Wang et al. | |
| 5,469,859 A | 11/1995 | Tsoglin et al. | |
| 5,503,157 A | 4/1996 | Sramek | |
| 5,505,209 A | 4/1996 | Reining | |
| 5,529,072 A | 6/1996 | Sramek | |
| 5,615,689 A | 4/1997 | Kotler | |
| 5,642,734 A | 7/1997 | Ruben et al. | |
| 5,685,316 A | 11/1997 | Schookin et al. | |
| 5,817,030 A | 10/1998 | Tarjan et al. | |
| 6,015,393 A | 1/2000 | Hovland et al. | |
| 6,053,873 A | 4/2000 | Govari et al. | |
| 6,073,039 A * | 6/2000 | Berson | 600/372 |
| 6,076,015 A | 6/2000 | Hartley et al. | |
| 6,142,941 A | 11/2000 | Benhalima et al. | |
| 6,298,267 B1 * | 10/2001 | Rosborough et al. | 607/6 |
| 6,304,773 B1 | 10/2001 | Taylor et al. | |
| 6,339,722 B1 | 1/2002 | Heethaar et al. | |
| 6,413,223 B1 | 7/2002 | Yang et al. | |
| 6,440,082 B1 | 8/2002 | Joo et al. | |
| 6,485,431 B1 | 11/2002 | Campbell et al. | |
| 6,496,732 B1 | 12/2002 | Wallace | |
| 6,511,438 B2 | 1/2003 | Bernstein et al. | |
| 6,577,897 B1 | 6/2003 | Shurubura et al. | |
| D625,823 S | 10/2010 | Schneider et al. | |
| 2002/0143368 A1 | 10/2002 | Bakels et al. | |
| 2002/0193689 A1 | 12/2002 | Bernstein et al. | |
| 2003/0083702 A1* | 5/2003 | Stadler et al. | 607/14 |
| 2003/0109790 A1 | 6/2003 | Stickney et al. | |
| 2003/0120170 A1 | 6/2003 | Zhu et al. | |
| 2003/0158584 A1* | 8/2003 | Cates et al. | 607/2 |
| 2003/0187341 A1 | 10/2003 | Sackner et al. | |
| 2003/0199779 A1 | 10/2003 | Muhlenberg et al. | |
| 2004/0102908 A1 | 5/2004 | Larson et al. | |
| 2004/0133123 A1 | 7/2004 | Leonhardt et al. | |
| 2005/0004609 A1 | 1/2005 | Stahmann et al. | |
| 2005/0043763 A1* | 2/2005 | Marcovecchio et al. | 607/5 |
| 2005/0124901 A1 | 6/2005 | Misczynski et al. | |
| 2005/0192488 A1 | 9/2005 | Bryenton et al. | |
| 2005/0217674 A1 | 10/2005 | Burton et al. | |
| 2006/0085048 A1 | 4/2006 | Cory et al. | |
| 2006/0122540 A1 | 6/2006 | Zhu et al. | |
| 2006/0200033 A1* | 9/2006 | Keren et al. | 600/504 |
| 2007/0191688 A1 | 8/2007 | Lynn | |
| 2008/0154116 A1* | 6/2008 | Duensing et al. | 600/410 |
| 2008/0255433 A1 | 10/2008 | Prough et al. | |
| 2009/0048497 A1 | 2/2009 | Keren | |
| 2010/0069765 A1 | 3/2010 | Keren | |
| 2011/0218419 A1 | 9/2011 | Keren et al. | |
| 2013/0144177 A1 | 6/2013 | Keren et al. | |

FOREIGN PATENT DOCUMENTS

| | | |
|---|---|---|
| WO | WO 2004/098376 | 11/2004 |
| WO | WO 2004/112606 | 12/2004 |
| WO | WO 2006/087696 | 8/2006 |
| WO | WO 2007/096054 | 8/2007 |
| WO | WO 2008/102362 | 8/2008 |
| WO | WO 2008/107899 | 9/2008 |
| WO | WO 2008/129535 | 10/2008 |
| WO | WO 2009/022330 | 2/2009 |

OTHER PUBLICATIONS

Response Dated Dec. 29, 2010 to Notice of Reason for Rejection of Sep. 17, 2010 From the Japanese Patent Office Re. Application No. 2006-507622.

Communication Pursuant to Article 94(3) EPC Dated Jan. 26, 2011 From the European Patent Office Re.: Application No. 04731993.4.

Response Dated Jan. 30, 2011 to Communication Pursuant to Article 94(3) EPC of Oct. 20, 2010 From the European Patent Office Re. Application No. 08719934.5.

Communication Pursuant to Article 94(3) EPC Dated Feb. 13, 2012 From the European Patent Office Re. Application No. 08789780.7.

Requisition by the Examiner Dated Jan. 9, 2012 From the Canadian Intellectual Property Office Re. Application No. 2,525,443.

Communication Pursuant to Article 94(3) EPC Dated Feb. 13, 2012 From the European Patent Office Re.: Application No. 08710233.1.

Communication Pursuant to Article 94(3) EPC Dated Feb. 13, 2012 From the European Patent Office Re. Application No. 08719934.5.

Communication Pursuant to Article 94(3) EPC Dated May 14, 2012 From the European Patent Office Re.: Application No. 04731993.4.

Requisition by the Examiner Dated May 30, 2012 From the Canadian Intellectual Property Office Re. Application No. 2,597,264.

Response Dated Jun. 3, 2010 to Communication Pursuant to Article 94(3) EPC of Feb. 12, 2010 From the European Patent Office Re.: Application No. 08738211.5.

Restriction Official Action Dated Jun. 7, 2012 From the US Patent and Trademark Office Re. U.S. Appl. No. 11/889,395.

Invitation Pursuant to Rule 62a(1) EPC Dated Jun. 10, 2010 From the European Patent Office Re. Application No. 06700959.7.

Official Action Dated Jun. 22, 2010 From the US Patent and Trademark Office Re.: U.S. Appl. No. 10/556,483.

Response Dated Jun. 28, 2010 to Communication Pursuant to Article 94(3) EPC of Dec. 29, 2009 From the European Patent Office Re.: Application No. 08710233.1.

Response Dated Jul. 4, 2010 to Invitation Pursuant to Rule 62a(1) EPC of Jun. 10, 2010 From the European Patent Office Re. Application No. 06700959.7.

Translation of Official Querry Dated Jul. 1, 2011 From the Japanese Patent Office Re. Application No. 2006-507622.

Response Dated Jul. 21, 2010 to Notice of Reason for Rejection of Apr. 6, 2010 From the Japanese Patent Office Re. Application No. 2006-507622.

Translation of Notice of Reason for Rejection Dated Apr. 6, 2010 From the Japanese Patent Office Re. Application No. 2006-507622.

Response Dated Jul. 25, 2011 to Communication Pursuant to Article 94(3) EPC of Jan. 26, 2011 From the European Patent Office Re.: Application No. 04731993.4.

Official Action Dated Aug. 31, 2011 From the US Patent and Trademark Office Re. U.S. Appl. No. 11/884,227.

Response Dated Sep. 11, 2011 to Official Querry Dated Jul. 1, 2011 From the Japanese Patent Office Re. Application No. 2006-507622.

Response Dated Sep. 12, 2011 to Official Action of Aug. 31, 2011 From the US Patent and Trademark Office Re. U.S. Appl. No. 11/884,227.

Communication Under Rule 71(3) EPC Dated Oct. 7, 2011 From the European Patent Office Re.: Application No. 08738211.5.

Response Dated Sep. 21, 2010 to Official Action of Jun. 22, 2010 From the US Patent and Trademark Office Re.: U.S. Appl. No. 10/556,483.

Translation of Notice of Reason for Rejection Dated Sep. 17, 2010 From the Japanese Patent Office Re. Application No. 2006-507622.

Communication Pursuant to Article 94(3) EPC Dated Oct. 20, 2010 From the European Patent Office Re. Application No. 08719934.5.

Official Action Dated Nov. 2, 2011 From the US Patent and Trademark Office Re. U.S. Appl. No. 11/884,227.

Delpierre et al. "Doppler Effect With Sound", Electronic Science Tutor, Retrieved From the Internet, 5 P., Oct. 18, 2011.

Ellis "Introduction to Mixers", Retrieved From the Internet, 9 P., 1999.
Response Dated Apr. 6, 2010 to Official Action of Oct. 6, 2009 From the US Patent and Trademark Office Re.: U.S. Appl. No. 10/556,483.
Written Opinion Dated Mar. 22, 2005 From the International Searching Authority Re.: Application No. PCT/Il04/00395.
Raza et al. "Filtering Respiration and Low-Frequency Movement Artefacts From the Cardiogenic Electrical Impedance Signal", Medical and Biological Engineering and Computing, XP000323425, 30(5): 556-561, Sep. 1, 1992. p. 556, r-h col., § 3—p. 557, r-h col., § 1, p. 557, 1-h col., § 3, p. 558, 1-h col., § 2-r-h col., § 1, Fig.3.
Saarelainen et al. "Whole-Body Impedance Recording—A Practical Method for the Diagnosis of Sleep Apnoea", Clinical Physiology and Functional Imaging, X0002488466, 23(2): 110-113, Mar. 2003.
Response Dated Nov. 17, 2011 to Examiner's Report of Nov. 15, 2010 From the Australian Government, IP Australia Re. Application No. 2006215274.
Notice of Allowability Dated Nov. 21, 2012 From the US Patent and Trademark Office Re. U.S. Appl. No. 11/884,227.
Communication Pursuant to Article 94(3) EPC Dated Jul. 8, 2009 From the European Patent Office Re.: Application No. 04731993.4.
Communication Relating to the Results of the Partial International Search Dated Dec. 5, 2008 From the International Searching Authority Re.: Application No. PCT/IL2008/001105.
International Preliminary Report on Patentability Dated Nov. 4, 2009 From the International Preliminary Examining Authority Re.: Application No. PCT/IL2008/001105.
International Preliminary Report on Patentability Dated Aug. 16, 2007 From the International Preliminary Examining Authority Re.: Application No. PCT/IL06/00075.
International Preliminary Report on Patentability Dated Sep. 17, 2009 From the International Bureau of WIPO Re.: Application No. PCT/IL2008/000309.
International Preliminary Report on Patentability Dated Nov. 18, 2008 From the International Preliminary Examing Authority Re.: Application No. PCT/IL04/00395.
International Preliminary Report on Patentability Dated Aug. 26, 2009 From the International Bureau of WIPO Re.: Application No. PCT/IL2008/000233.
International Preliminary Report on Patentability Dated Oct. 29, 2009 From the International Bureau of WIPO Re.: Application No. PCT/IL2008/000509.
International Search Report Dated Aug. 5, 2008 From the International Searching Authority Re.: Application No. PCT/IL2008/000309.
International Search Report Dated Dec. 6, 2006 From the International Searching Authority Re.: Application No. PCT/IL06/00075.
International Search Report Dated Mar. 22, 2005 From the International Searching Authority Re.: Application No. PCT/IL04/00395.
International Search Report Dated Mar. 27, 2009 From the International Searching Authority Re.: Application No. PCT/IL2008/001105.
International Search Report Dated Jul. 28, 2008 From the International Searching Authority Re.: Application No. PCT/IL2008/000233.
Office Action Dated Dec. 12, 2008 From the State Intellectual Property Office of the People's Republic of China Re.: Application No. 200680012560.2.
Office Action Dated Apr. 24, 2009 From the State Intellectual Property Office of the People's Republic of China Re.: Application No. 200480019436.X.
Office Action Dated Jul. 24, 2009 From the State Intellectual Property Office of the People's Republic of China Re.: Application No. 200680012560.2 and Its Translation Into English.
Official Action Dated Oct. 6, 2009 From the US Patent and Trademark Office Re.: U.S. Appl. No. 10/556,483.
Official Action Dated Feb. 18, 2009 From the US Patent and Trademark Office Re.: U.S. Appl. No. 10/556,483.
Response Dated Nov. 8, 2009 to Communication Pursuant to Article 94(3) EPC of Jul. 8, 2009 From the European Patent Office Re.: Application No. 04731993.4.
Supplementary Partial European Search Report Dated Apr. 9, 2009 From the European Patent Office Re.: Application No. 04731993.4.
Translation of the Official Action Dated Dec. 12, 2008 From the State Intellectual Property Office of the People's Republic of China Re.: Application No. 200680012560.2.
Written Opinion Dated Aug. 5, 2008 From the International Searching Authority Re.: Application No. PCT/IL2008/000309.
Written Opinion Dated Dec. 6, 2006 From the International Searching Authority Re.: Application No. PCT/IL06/00075.
Written Opinion Dated Mar. 22, 2005 From the International Searching Authority Re.: Application No. PCT/I104/00395.
Written Opinion Dated Mar. 27, 2009 From the International Searching Authority Re.: Application No. PCT/IL2008/001105.
Written Opinion Dated Jul. 28, 2008 From the International Searching Authority Re.: Application No. PCT/IL2008/000233.
Bakshi et al. "Circulatory Response in Sleep Apnea Patients During Sleep Before and After CPAP Treatment", Sleep, XO008094214, 28(Suppl.S): A194: 0576, 2005. 19th Annual Meeting of the Associated-Professional-Sleep-Societies, Denver, CO, USA, Jun. 18-23, 2005. Abstract.
Goovaerts et al. "A Wideband High Common Mode Rejection Ratio Amplifier for Multifrequency Impedance Measurement", Medical and Biological Engineering and Computing, XP000784850, 36(6): 761-767, Nov. 1, 1998. Section 2.2 'Lock-in Measurement', p. 761, p. 763, col. 2, Figs.2, 3.
Jellinek et al. "Right Atrial Pressure Predicts Hemodynamic Response to Apneic Positive Airway Pressure", Critical Care Medicine, XP002488470, 28(3): 672-678, Mar. 2000. Database MEDLINE [Online], US National Library of Medicine, Database Accession No. NLM10752813. Abstract.
Kubicek et al. "The Minnesota Impedance Cardiograph—Theory and Applications", Biomedical Engineering, XP001051054, 9(9): 410-416, Sep. 1, 1974. p. 411, Middle Col., Figs.1, 2.
Lele et al. "Exercise Capacity in Hypertrophic Cardiomyopathy. Role of Stroke Volume Limitation, Heart Rate, and Diastolic Filling Characteristics", Circulation, XP002487808, 92(10): 2886-2894, 1995.
Lin et al. "Effects of Hypercapnia, Hypoxia, and Rebreathing on Circulatory Response to Apnea", Journal of Applied Physiology Respiratory Environmental and Exercise Physiology, XP008094195, 54(1): 172-177, 1983.
Miyamoto et al. "Cardiorespiratory Dynamics During Sinusoidal and Impulse Exercise in Man", Japanese Journal of Physiology, XP008094022, 33(6): 971-986, 1983.
Myers et al. "Cardiac Output and Cardiopulmonary Responses to Exercise in Heart Failure: Application of a New Bio-Resistance Device", Journal of Cardiac Failure, XP0022287174, 13(8): 629-636, Oct. 6, 2007.
Newman et al. "The Non-Invasive Assessment of Stroke Volume and Cardiac Output by Impedance Cardiography: A Review", Aviation Space and Environmental Medicine, XP008093991, 70(8): 780-789, Aug. 1999.
Raza et al. "Filtering Respiration and Low-Frequency Movement Artefacts From the Cardiogenic Electrical Impedance Signal", Medical and Biological Engineering and Computing, XP000323425, 30(5): 556-561, Sep. 1, 1992. p. 556, r-h col., § 3—p. 557, r-h col., § 1, p. 557, 1-h col., § 3, p. 558, 1-h col., § 2-r-h col., § 1, Fig.3.
Saarelainen et al. "Whole-Body Impedance Recording—A Practical Method for the Diagnosis of Sleep Apnoea", Clinical Physiology and Functional Imaging, XO002488466, 23(2): 110-113, Mar. 2003.
Schumacker et al. "Oxygen Delivery and Uptake Relationships in Patients With Aortic Stenosis", American Journal of Respiratory and Critical Care Medicine, XP002488468, 149(5): 1123-1131, May 1994. Database EMBASE [Online], Database Accession No. EMB-1994152503, 1994. Abstract.
Stoohs et al. "Cardiovascular Changes Associated With Obstructive Sleep Apnea Syndrome", Journal of Applied Physiology, XP002488467, 72(2): 583-589, 1992. Database Biosis [Online], Biosciences Information Service, Database Accession No. PREV199293105800, 1992. Abstract.
Tolle et al. "Reduced Stroke Volume Related to Pleural Pressure in Obstructive Sleep Apnea", Journal of Applied Physiology Respiratory Environmental and Exercise Physiology, XP002488469, 55(6): 1718-1724, 1983. Database BIOSIS [Online], Biosciences Information Service, Database Accession No. PREV198477063246, 1883. Abstract.

Communication Pursuant to Article 94(3) EPC Dated Dec. 29, 2009 From the European Patent Office Re.: Application No. 08710233.1.
Communication Pursuant to Article 94(3) EPC Dated Feb. 12, 2010 From the European Patent Office Re.: Application No. 08738211.5.
Official Action Dated Jul. 10, 2012 From the US Patent and Trademark Office Re. U.S. Appl. No. 12/527,697.
Official Action Dated Aug. 2, 2012 From the US Patent and Trademark Office Re. U.S. Appl. No. 11/884,227.
Communication Under Rule 71(3) EPC Dated Oct. 17, 2012 From the European Patent Office Re. Application No. 08789780.7.
Official Action Dated Oct. 23, 2012 From the US Patent and Trademark Office Re. U.S. Appl. No. 12/450,022.
Patent Examination Report Dated Nov. 30, 2012 From the Australian Government, IP Australia Re. Application No. 2008288084.
Official Action Dated Aug. 9, 2012 From the US Patent and Trademark Office Re. U.S. Appl. No. 11/889,395.
Requisition by the Examiner Dated Jul. 24, 2012 From the Canadian Intellectual Property Office Re. Application No. 2,525,443.
Applicant—Initiated Interview Summary Dated Sep. 17, 2012 From the US Patent and Trademark Office Re. U.S. Appl. No. 11/884,227.
Notice of Allowance Dated Oct. 25, 2012 From the US Patent and Trademark Office Re. U.S. Appl. No. 11/884,227.
Official Action Dated Oct. 15, 2012 From the US Patent and Trademark Office Re. U.S. Appl. No. 12/673,037.
Official Action Dated Apr. 9, 2013 From the US Patent and Trademark Office Re. U.S. Appl. No. 12/527,697.
Patent Examination Report Dated Aug. 1, 2012 From the Australian Government, IP Australia Re. Application No. 2008242145.
Notice of Allowance Dated Jan. 30, 2013 From the US Patent and Trademark Office Re.: U.S. Appl. No. 10/556,483.
Official Action Dated Jun. 17, 2013 From the US Patent and Trademark Office Re. U.S. Appl. No. 12/450,022.
Official Action Dated Jun. 26, 2013 From the US Patent and Trademark Office Re. U.S. Appl. No. 12/527,697.
Restriction Official Action Dated Jul. 3, 2013 From the US Patent and Trademark Office Re. U.S. Appl. No. 13/757,920.

* cited by examiner

METHOD, APPARATUS AND SYSTEM FOR PREDICTING ELECTROMECHANICAL DISSOCIATION

RELATED APPLICATIONS

This Application is a National Phase of PCT Patent Application No. PCT/IL2008/000509 having International filing date of Apr. 15, 2008, which is a continuation-in-part of U.S. patent application Ser. No. 11/889,395 filed on Aug. 13, 2007.

PCT Patent Application No. PCT/IL2008/000509 also claims the benefit of U.S. Provisional Patent Application No. 60/907,847 filed on Apr. 19, 2007. The contents of the above Applications are all incorporated herein by reference.

FIELD AND BACKGROUND OF THE INVENTION

The present invention, in some embodiments thereof, relates to cardiovascular medical applications and, more particularly, but not exclusively, to a method, apparatus and system for predicting electro-mechanical dissociation or pulseless electrical activity.

Sudden cardiac arrest is a life-threatening condition. It is recognized that the percentage of individuals who are successfully resuscitated with intact neurological function following a sudden cardiac arrest is less than 10%.

A cardiac arrest is the cessation of normal circulation of the blood due to failure of the ventricles of the heart to contract effectively resulting in the cessation of blood delivery to the whole body. As a consequence cells of the whole body suffer injury resulting from hypoxia (oxygen starvation). Lack of oxygen supply to the brain causes victims to immediately lose consciousness and shortly thereafter stop breathing. Cardiac arrest is different from a heart attack (myocardial infarction). In a cardiac arrest the heart suddenly stops beating. In a heart attack, blood flow to a region of the heart muscle is disrupted. That region of the heart muscle deprived of blood flow suffers injury which might lead to cell death if blood flow is not restored promptly. During a heart attack, only part of the heart ceases to work properly, thereby compromising cardiac function, but not completely; the rest of the heart muscle continues to work promoting blood flow albeit the total work produced by the heart may be sometimes significantly diminished. However, heart attacks can sometimes lead to cardiac arrest in which the heart as a whole stops beating and ceases to promote blood flow into the systemic circulation.

In apparently healthy adults, cardiac arrest is often precipitated by ventricular fibrillation, which is most often associated with underlying coronary artery disease, but may also be associated with electrical abnormalities of the heart muscle originating in a region of the heart in which there is reduction of blood flow or disproportionate increase in oxygen demands in such region.

Cardiac arrest can also occur without ventricular fibrillation. The heart can stop beating because of asystole in which there are no electrical impulses originating from the heart, or because of Electromechanical Dissociation (EMD) which is a clinical condition with no palpable pulse or blood flow although coordinated ventricular electrical activity exists. During EMD, there is an adequate cardiac electrical rhythm but no effective cardiac pump action by the heart, so that no significant arterial pressure is generated spontaneously. Recently, the term Pulseless Electrical Activity (PEA) has been used for this condition.

There are numerous reasons leading up to EMD. Oftentimes the reason relates to a severe systemic condition which affects the heart as a component of multi organ failure. For example, EMD may occur in patients with severe septic syndrome, severe hemodynamic instability such as hypovolemic shock, severe metabolic acidosis, severe hypoglycemia, disseminated cancer and so on. In those cases, despite an electrical trigger to contract that heart's muscle cells (e.g., myocardium) fail to contract. For example, in severe acidosis the pH environment disrupts the normal contraction of myocardial cells; while in severe shock myocardial cells suffer form poor perfusion and hypoxia. In some cases, EMD occurs following treatment with a defibrillator, where a patient may exhibit an electrical pulse but not a physical pulse. It has been reported that less than 10% of individuals with post-shock EMD survive.

Cardiac arrest caused by asystole or pulseless electrical activity can also occur associated with existing cardiac disease, especially when severe heart failure has developed.

U.S. Pat. No. 6,440,082 to Joo et al., discloses a technique in which phonocardiogram (PCG) data electrocardiogram (ECG) data are analyzed for determining the presence of a pulse in the patient and determining whether the patient is in a state of PEA. The PCG data are evaluated to indicate the presence of a heart sound, and the ECG data are evaluated to indicate the presence of a QRS complex. If the time at which the QRS complex occurs is within an expected time of when the heart sound appeared to occur, a cardiac pulse is determined to be present in the patient. Joo et al. also disclose a technique in which the ECG data are evaluated to gate the heart sound detection process. Specifically, Joo et al. teach that if a heart sound is not detected following an R-wave, the patient may be in a state of PEA.

U.S. Published Application No. 20030109790 to Stickney et al. discloses a technique in which PEA is detected when a patient is determined pulseless and the patient is not experiencing ventricular defibrillation, ventricular tachycardia or asystole. According to Stickney et al., the presence or absence of a cardiac pulse is determined by evaluating fluctuations in an electrical signal that represents a measurement of the patient's transthoracic impedance; the presence or absence of ventricular defibrillation or tachycardia is determined by differentiating shockable from non-shockable cardiac rhythms according to the teachings of U.S. Pat. No. 4,610,254; and the presence or absence of is determined according to the teachings of U.S. Pat. No. 6,304,773. Stickney et al. also teach detection of PEA using ECG data wherein a state of PEA is detected when QRS complexes are repeatedly observed without detection of a cardiac pulse associated therewith.

SUMMARY OF THE INVENTION

Some embodiments of the present invention predict onset of electromechanical dissociation in a heart of a subject using a composite input electrical signal received from the subject. An electrocardiac signal and a radiofrequency signal are extracted from the composite signal. Based on the electrocardiac signal, the electrical activity of the heart is determined. Based on the radiofrequency signal, one or more blood flow measures are determined. Onset of electromechanical dissociation (EMD) or pulseless electrical activity (PEA) is predicted according to predetermined criteria which depend on the electrical activity and blood flow measure(s).

Unlike traditional techniques which only provide post occurrence identification of electromechanical dissociation, some embodiments of the present invention predicts the onset of electromechanical dissociation ahead of time. This can be achieved by a judicious selection of the criteria for the prediction. Specifically, according to the present embodiments, impending onset of electromechanical dissociation is likely to occur, if the flow rate characterizing the mechanical activity of the heart is markedly reduced, while the rhythm characterizing the electrical activity of the heart remains above another predetermined threshold.

Thus, according to an aspect of some embodiments of the present invention there is provided a method of predicting onset of electromechanical dissociation in a heart of a subject. The method comprises: extracting from the composite input signal an electrocardiac signal and determining electrical activity of the heart based on the electrocardiac signal; extracting from the composite input signal a radiofrequency signal and determining blood flow measure based on the radiofrequency signal; and if the blood flow measure is below a predetermined threshold and the electrical activity is above a predetermined threshold, then predicting the onset of electromechanical dissociation. The method can also identify electromechanical dissociation which is already in effect when there is no or minimal blood flow. Thus, when the method determines that the blood flow measure is below the predetermined threshold, it can further compare the blood flow measure to an additional, lower, threshold. If the blood flow measure is even below the additional threshold, the method can identify that electromechanical dissociation is already in effect and, e.g., generates an alarm signal.

According to an aspect of some embodiments of the present invention there is provided a method of predicting onset of electromechanical dissociation in a heart of a subject. The method comprises transmitting output radiofrequency signals to the subject, receiving a composite input electrical signal from the subject, and executing the method described above.

According to some embodiments of the invention the method further comprises reducing or eliminating amplitude modulation of the radiofrequency component so as to provide a signal of substantially constant envelope.

According to some embodiments of the present invention the method further comprises filtering the radiofrequency signal using a dynamically variable filter.

According to an aspect of some embodiments of the present invention there is provided apparatus for predicting onset of electromechanical dissociation in a heart of a subject. The apparatus comprises: an input unit for receiving a composite input electrical signal from the subject; an electrocardiac unit for extracting from the composite input signal an electrocardiac signal and determining electrical activity of the heart based on the electrocardiac signal; a radiofrequency unit for extracting a radiofrequency signal from the composite input signal and determining blood flow measure based on the radiofrequency signal. The apparatus also comprises an output unit for outputting a signal predicting the onset of electromechanical dissociation if the blood flow measure is below a predetermined threshold and the electrical and activity is above a predetermined threshold.

According to an aspect of some embodiments of the present invention there is provided a system for predicting onset of electromechanical dissociation in a heart of a subject. The system comprises a radiofrequency generator for generating output radiofrequency signals, a plurality of electrodes designed for transmitting the output radiofrequency signals to the subject and for sensing a composite input electrical signal from the subject, and the apparatus described above.

According to some embodiments of the present invention the apparatus further comprises an envelope elimination unit designed and configured for reducing or eliminating amplitude modulation of the radiofrequency signal so as to provide a radiofrequency signal of substantially constant envelope.

According to some embodiments of the present invention the apparatus further comprises a filtering unit configured for filtering the radiofrequency signal using dynamically variable filter.

According to some embodiments of the present invention the dynamically variable filter is adapted in response to a change in a physiological condition of the subject.

According to some embodiments of the invention the physiological condition is a heart rate of the subject.

According to some embodiments of the invention a lower frequency bound characterizing the filter is about $0.9*(HR/60)$ Hz at all times, wherein the HR is the heart rate in units of beats per minute.

According to some embodiments of the invention an upper frequency bound characterizing the filter is about $6+1.5*[(HR/60)-1]$ Hz at all times, wherein the HR is the heart rate in units of beats per minute.

According to some embodiments of the present invention the electrocardiac signal comprises an ECG signal. According to some embodiments of the invention the determination of the electrical activity comprises determination of a QRS rate from the ECG signal.

According to some embodiments of the present invention the blood flow measure comprises cardiac output. According to some embodiments of the invention the onset of electromechanical dissociation is predicted if the cardiac output is reduced by at least 50% over a period of about five minutes and the electrical activity is characterized by a pulse rate of at least 40 pulses per minute.

According to some embodiments of the invention the onset of electromechanical dissociation is predicted if the cardiac output is less than 1 liter per minute over a period of about five minutes and the electrical activity is characterized by a rhythm of at least 40 cycles per minute.

According to some embodiments of the present invention the blood flow measure comprises cardiac index. According to some embodiments of the invention the onset of electromechanical dissociation is predicted if the cardiac index over a period of about five minutes is less than 1 more preferably less than 0.75 liter per minute per square meter and the electrical activity is characterized by a rhythm of at least 40 cycles per minute.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
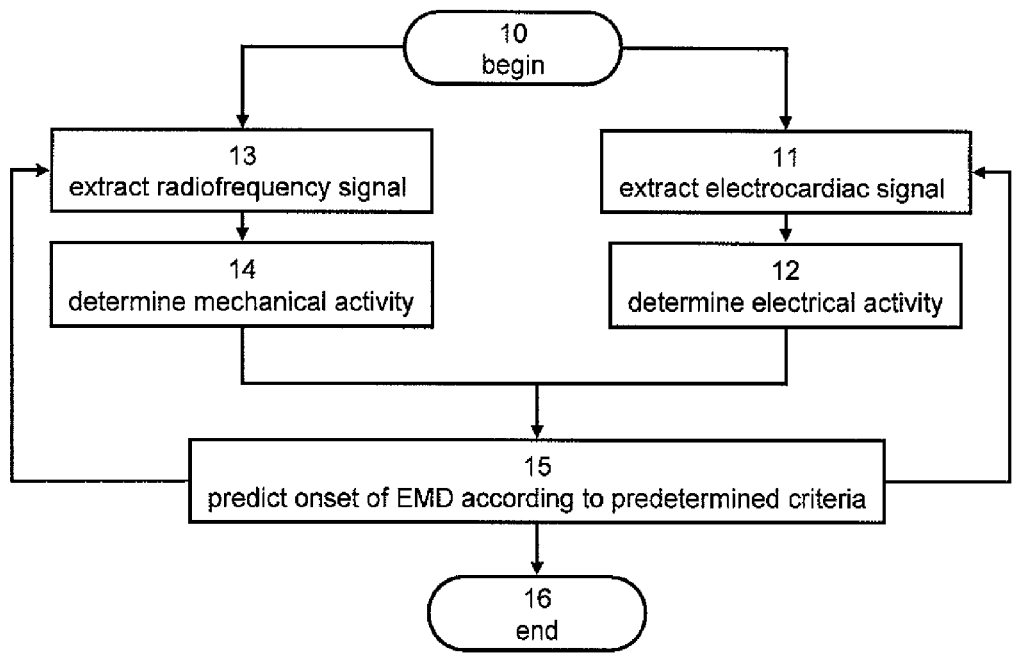
FIGS. 1a-b are flowchart diagrams illustrating a method suitable for predicting onset of electromechanical dissociation in a heart of a subject, according to various exemplary embodiments of the present invention.

The present invention, in some embodiments thereof, relates to cardiovascular medical applications and, more particularly, but not exclusively, to a method, apparatus and system for predicting electro-mechanical dissociation.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Computer programs implementing the method according to embodiments of the present invention can commonly be distributed to users on a distribution medium such as, but not limited to, a floppy disk, CD-ROM and flash memory cards. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The method, apparatus and system of the present embodiments are particularly useful for predicting a possibility of a future onset of electromechanical dissociation in the heart of a subject. Yet, the use of the present embodiments in other situations, such as the identification of electromechanical dissociation onset, is not excluded from the scope of the present invention.

It was found by the present inventors that the onset of electromechanical dissociation can be predicted ahead of time, unlike traditional techniques which only provide post occurrence identification of electromechanical dissociation. The present embodiments predict electromechanical dissociation onset by providing a quantitative estimate of the mechanical activity of the heart while monitoring its electrical activity. Specifically, according to the present embodiments onset of electromechanical dissociation is likely to occur, if the flow rate characterizing the mechanical activity of the heart is lower then one predetermined threshold while the rhythm characterizing the electrical activity of the heart remains above another predetermined threshold.

Referring now to the drawings, FIG. 1a is a flowchart diagram illustrating a method suitable for predicting onset of electromechanical dissociation in a heart of a subject, according to various exemplary embodiments of the present invention.

It is to be understood that, unless otherwise defined, the method steps described hereinbelow can be executed either contemporaneously or sequentially in many combinations or orders of execution. Specifically, the ordering in each flowchart diagram of this specification is not to be considered as limiting. For example, two or more method steps, appearing in the following description or in a flowchart diagram in a particular order, can be executed in a different order (e.g., a reverse order) or substantially contemporaneously. Additionally, several method steps described below are optional and may not be executed.

Generally, the method of the present embodiments uses a composite input electrical signal received from the subject. The composite input electrical signal typically includes a radiofrequency signal pertaining to the blood flow in the heart, and an electrocardiac signal pertaining to electrical activity in the myocardium.

With reference to FIG. 1a, at 10 the method begins and at 11 the electrocardiac signal is extracted from the composite input signal. The electrocardiac signal can be an electrocardiogram (ECG) signal or a signal which correlates with an ECG signal. Typically, the electrocardiac signal comprises a DC signal or a signal characterized by very low frequency (less than 150 Hz). ECG signals, for example, are typically characterized by amplitudes of 0.1-5 mV and frequencies of 0.05-130 Hz.

The extraction of DC signal or a very low frequency signal can be done using a suitable electronic circuitry or device which receives the composite signal and filter out high frequency (typically radiofrequency) components. Such electronic circuitries are known in the art. For example, a feedback capacitor or an integrator type electronic circuitry can be constituted to extract the electrocardiac signal. Optionally, the electronic circuitry can amplify the electrocardiac signal as known in the art.

At 13 the radiofrequency signal is extracted from the composite input signal. The extraction of the radiofrequency component from the composite input signal can be done using a suitable electronic circuitry or device which receives the composite signal and filter out low frequency components. Such electronic circuitries are known in the art. For example, a serial capacitor or a differentiator type electronic circuitry can be constituted to extract radiofrequency signal. Optionally the electronic circuitry amplifies the radiofrequency signal as known in the art.

Method steps 11 and 13 can be performed in any order of execution. In various exemplary embodiments of the invention method steps 11 and 13 are executed simultaneously.

At 12 the method determines the electrical activity of the heart based on the electrocardiac signal. Preferably, but not obligatorily the method attempts to identify one or more repetitive patterns in the electrocardiac signal and determines the repetition rate of the identified patterns. For example, when the electrocardiac signal is an ECG signal, the method can identify the QRS complex in the ECG signal and determine the QRS rate (e.g., by measuring the RR interval and defining the rate as the inverse of the RR interval).

At 14 the method determines the mechanical activity of the heart based on the radiofrequency signal. The mechanical activity is preferably expressed in terms of one or more blood flow measures, such as, but not limited to, cardiac output, cardiac index, stroke volume and the like. The determination of blood flow measure from the obtained radiofrequency signal can be done using any procedure known in the art. Some procedures for calculating blood flow measures in accordance with embodiments of the present invention are provided hereinunder.

Method steps 12 and 14 can be performed in any order of execution. In various exemplary embodiments of the invention method steps 12 and 14 are executed simultaneously.

At 15 the method predicts the onset of electromechanical dissociation (EMD) or Pulseless Electrical Activity (PEA) according to predetermined criteria. The criteria are preferably based on the electrical and mechanical activities as determined at 12 and 14. Generally, when the electrical activity is normal and the mechanical activity is below normal (taking into account to the age, size, weight and gender of the subject), the method predicts onset of EMD or PEA.

Figure 1B:
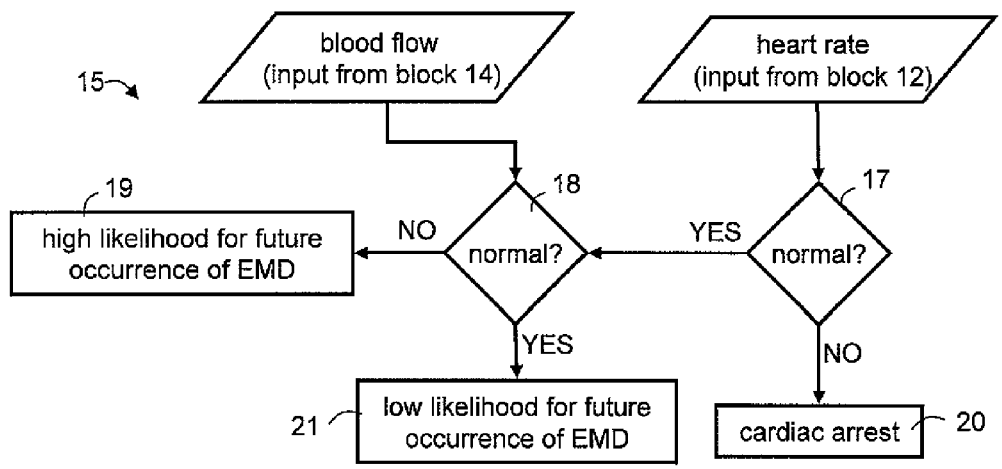

A representative example of a set of criteria suitable for step 15 is illustrated in FIG. 1b. In decision block 17 the method determines, over a predetermined period of time, whether or not the heart rate, as determined from the electrocardiac signal (see block 12 in FIG. 1a), is normal. This can be done by comparing the measured rate to a predetermined threshold. For example, the threshold can be about 40 beats per minute, in which case any heart rate above 40 beats per minute can be defined as "normal" and any heart rate below 40 beats per minute can be defined as "below normal." The threshold can also be higher than 40 beats per minute. Preferably the threshold is from about 40 beats per minute to about 60 beats per minute.

As used herein the term "about" refers to ±10%.

If the heart rate is below normal, the method identifies cardiac arrest (block 20) and preferably generates a cardiac arrest warning signal (not shown in FIG. 1b).

If the heart rate is normal, the method proceeds to decision step 18 where the method determines, over the predetermined time period, whether or not the blood flow measure, as determined from the radiofrequency signal (see block 14 in FIG. 1a), is normal. This can be done by comparing the calculated blood flow measure to a predetermined threshold, which can be expressed either in absolute value or as a percentage of the characteristic blood flow of the subject. For example, when the blood flow measure is cardiac output the predetermined threshold can be about X liters per minute, where X is a number ranging from about 1 to about 1.5. In this embodiment, any cardiac output less than X is defined as "below normal". Alternatively, the method can define a baseline cardiac output for the subject and compare the instantaneous cardiac output to the baseline. In this embodiment, the cardiac output can be defined as "below normal" whenever it drops below 70% or 60% or 50% of the baseline.

When the blood flow measure is cardiac index (cardiac output per unit surface area of the subject's body) the predetermined threshold can be about Y liters per minute per square meter, where Y is a number ranging from about 0.75 to about 1. In this embodiment, any cardiac index below Y is defined as "below normal". Alternatively, the method can define a baseline cardiac index for the subject and compare the instantaneous cardiac index to the baseline, wherein the cardiac index can be defined as "below normal" whenever it drops below 70% or 60% or 50% of the baseline.

If the blood flow is below normal, the method determines that the likelihood for future occurrence of EMD is high (block 19). The method can also provides a quantified estimate of the likelihood (e.g., expressed as percentage), for example, based on the difference between the calculated blood flow and the characteristic blood flow of the subject. If the blood flow is normal (above the predetermined threshold) the method determines that the likelihood for future occurrence of EMD is low (block 21).

The predetermined time period over which the method compares the heart rate and blood flow measure to the thresholds is typically, but not obligatorily about five minutes. The comparison over this time period can be performed in continuous manner and a statistical procedure, such as a significance test can be employed during this period. Alternatively or additionally, the method can employ averaging procedure to determine an average blood flow measure and an average heart rate, and compare the averaged quantities to the respective thresholds.

The above procedure is preferably a continuous procedure wherein the method loops back and continuously extracts the electrocardiac and radiofrequency signals as shown in FIG. 1a, until a stop signal is received or until the composite input signal no longer exists.

The method ends at step 16.

Figure 2:
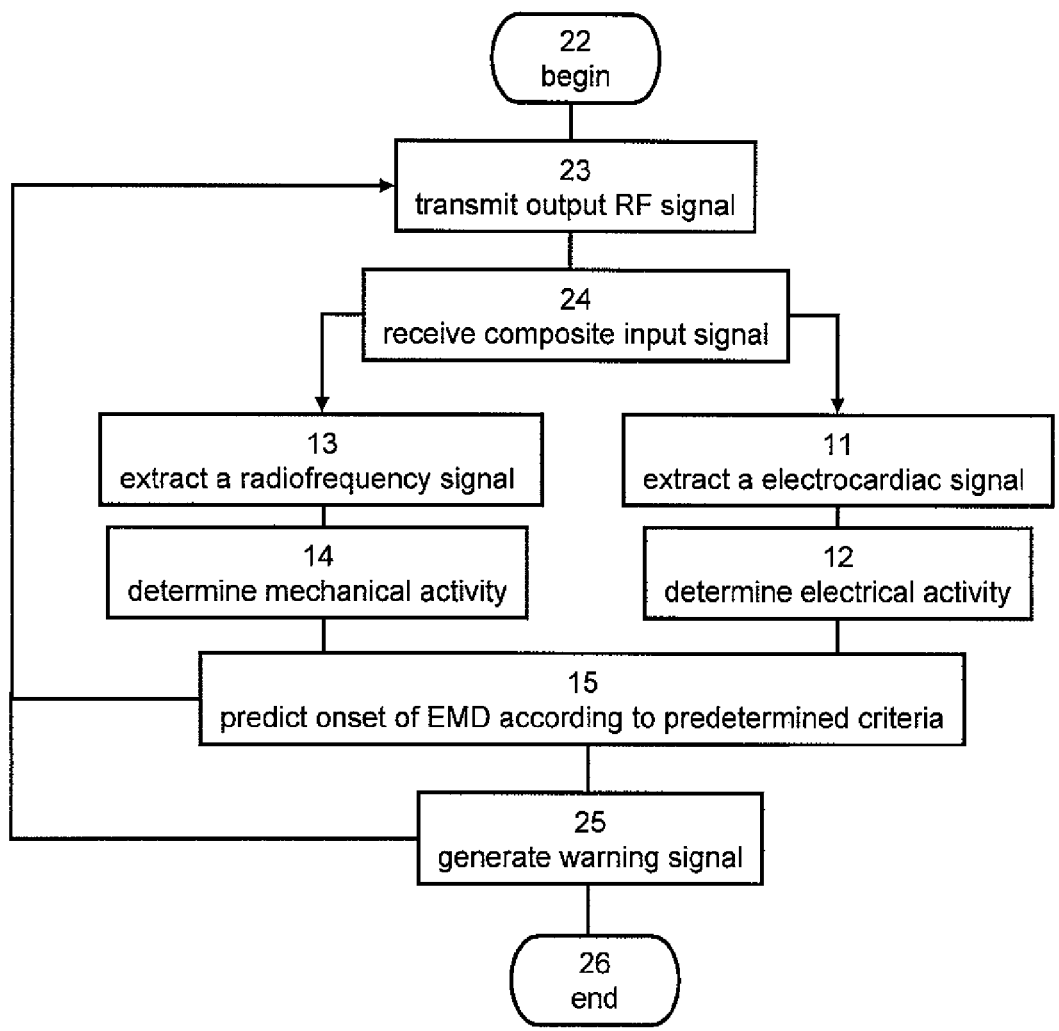
FIG. 2 is a flowchart diagram illustrating a more detailed method suitable for predicting onset of electromechanical dissociation in a heart of a subject, according to various exemplary embodiments of the present invention.

A more detailed method according to some embodiments of the present invention is illustrated in the flowchart diagram of FIG. 2.

The method begins at step 22 and optionally continues to step 23 in which output radiofrequency signals are transmitted to the subject, and step 24 in which an input composite signal is received from the subject. The output radiofrequency signals can be generated by a radiofrequency generator which generates a periodic high frequency current output in response to a periodic control input signal. The current output can be transmitted to the subject via an arrangement of electrodes for carrying current output from the radiofrequency generator as known in the art. The electrodes can be connected to locations of the body of the subject, e.g., above and below the heart.

Current, generated by the radiofrequency generator, flows across the thorax and causes a voltage drop due to the impedance of the body. In addition, action potentials originated from the sinoatrial node of the heart generate electrocardiac current which propagates along the myocardium. The electrodes sense a composite input signal which includes both the radiofrequency signal resulting from the flow of radiofrequency current across the thorax and the electrocardiac signal resulting from action potentials of the sinoatrial node.

The method continues to steps 11, 12, 13 and 14 in which the electrocardiac and radiofrequency signals are extracted and the electrical and mechanical activities of the heart are determined as further detailed hereinabove. The method continues to step 15 in which the method predicts EMD onset as further detailed hereinabove. When the method determines that EMD onset is likely to occur, the method preferably generates a warning signal (block 25), which can be accompanied by an alarm signal (audio and/or visual) sensible by the subject or others.

The method can loop back to step 23 for continuous transmission of output radiofrequency signals and monitoring of electrical and mechanical activity of the heart.

The method ends at step 26.

Figure 3:
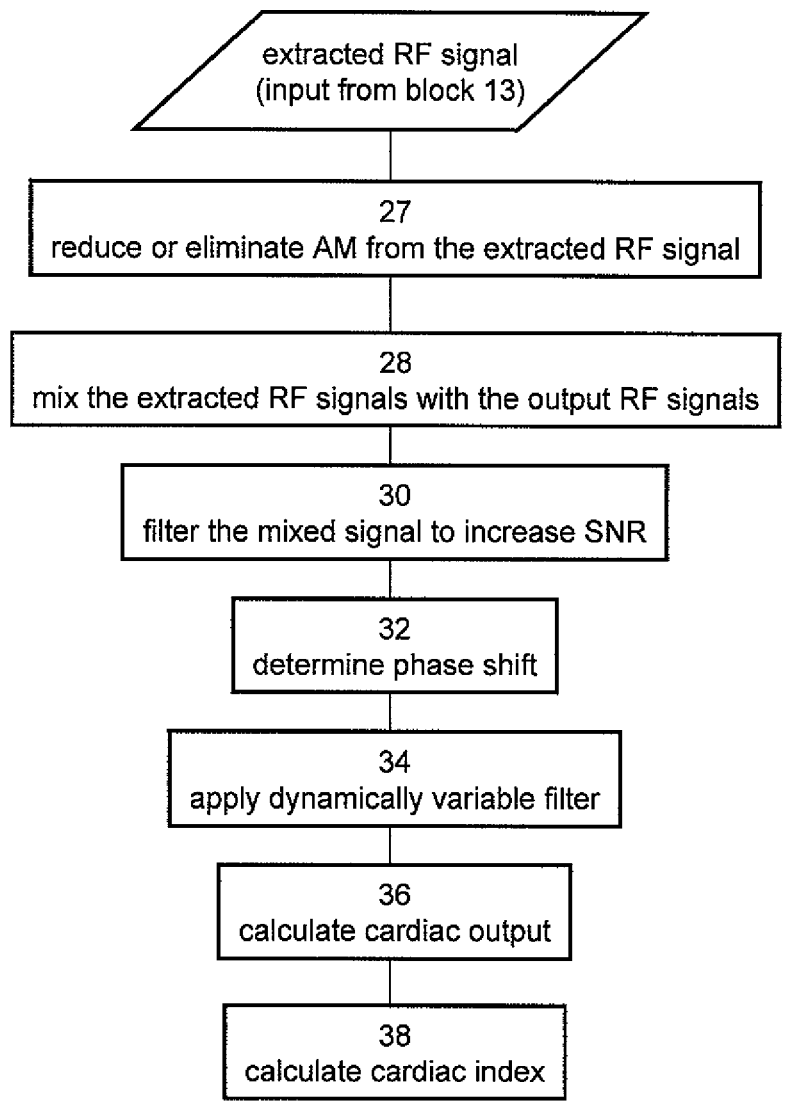
FIG. 3 is a flowchart diagram illustrating a procedure suitable for determining mechanical activity of the heart using a radiofrequency signal according to some embodiments of the present invention.

FIG. 3 is a flowchart diagram illustrating a procedure suitable for determining the mechanical activity using the radiofrequency signal which is extracted from the input composite signal according to some embodiments of the present invention. The procedure can be used for executing block 14 of the method described above.

The procedure uses the radiofrequency signal as extracted in step 13 of the method. Typically, but not obligatorily, the extracted radiofrequency signal relates to the hemodynamic reactance of the subject's thorax.

As used herein, "hemodynamic reactance" refers to the imaginary part of the impedance. Techniques for extracting the imaginary part from the total impedance are known in the art. Typically, such extraction is performed at hardware level but the use of algorithm at a software level is not excluded from the scope of the present invention.

In some embodiments of the present invention, the procedure reduces or, more preferably eliminates amplitude modulation of the extracted radiofrequency signals (block 27). Optionally and preferably the phase modulation of the signals is maintained. The extracted radiofrequency signals typically carry a substantial amount of AM noise, which can be described, without limitation as a signal $v(t)\cos(\omega t+\phi(t))$, which contains both phase and amplitude modulation. According to some embodiments the method generates signals having a substantial constant envelope, e.g., $v_0 \cos(\omega t+\phi(t))$, where $v_0$ is substantially a constant. The obtained signals thus represent the phase (or frequency) modulation of the extracted radiofrequency signal. The reduction or elimination of the amplitude modulation can be achieved, for example, using a limiter amplifier which amplifies the radiofrequency signals and limits their amplitude such that the amplitude modulation is removed.

In some embodiments, the procedure proceeds to step 28 in which the output radiofrequency signals are mixed with the extracted radiofrequency signals so as to provide a mixed radiofrequency signal. According to a preferred embodiment of the present invention, the mixed radiofrequency signal is composed of a plurality of radiofrequency signals, which may be, in one embodiment, a radiofrequency sum and a radiofrequency difference. A sum and a difference may be achieved, e.g., by multiplying the input and output signals. Since a multiplication between two frequencies is equivalent to a frequency sum and a frequency difference, the mix signal is composed of the desired radiofrequency sum and radiofrequency difference.

One ordinarily skilled in the art would appreciate that the advantage in the production of a radiofrequency sum and a radiofrequency difference is that whereas the radiofrequency sum includes both the signal and a considerable amount of electrical noise, the radiofrequency difference is approximately noise-free.

According to a preferred embodiment of the procedure continues to step 30 in which a portion of the mixed signal is filtered out such that a remaining portion of the mixed signal is characterized by a signal-to-noise ratio (SNR) which is substantially higher compared to the signal-to-noise ratio of the mixed signal or the extracted radiofrequency signal.

The procedure optionally and preferably continues to step 32 in which a phase shift $\Delta\phi$ of the extracted radiofrequency signals relative to the output radiofrequency signals is determined. It was found by the inventors of the present invention that the phase shift of the input signals, as received from the subject, relative to the output signals as generated by the radiofrequency generator, is indicative of the cardiac output of the subject.

The advantage of using $\Delta\phi$ for determining the cardiac output is that the relation between the blood flow and $\Delta\phi$ depends on fewer measurement-dependent quantities as compared to conventional determination techniques in which the impedance is used. The phase shift can be determined for any frequency component of the spectrum of extracted radiofrequency signals. For example, in one embodiment, the phase shift is determined from the base frequency component, in another embodiment the phase shift is determined from the second frequency component, and so on. Alternatively the phase shift can be determined using several frequency components, e.g., using an appropriate averaging algorithm.

In some embodiments of the present invention the procedure continues to step 34 in which a dynamically variable filter is applied. The dynamically variable filter filters the data according to a frequency band which is dynamically adapted in response to a change in the physiological condition of the subject. It was found by the Inventor of the present invention that the dynamical adaptation of the frequency band to the physiological condition of the subject can significantly reduce the influence of unrelated signals on the measured property.

Thus, in the present embodiment, step 34 includes a process in which first the physiological condition of the subject is determined, then a frequency band is selected based on the physiological condition of the subject, and thereafter the input signals or a portion thereof are filtered according to frequency band. The frequency band is dynamically adapted in response to a change in the physiological condition. The physiological condition is preferably, but not obligatorily, the heart rate of the subject, which can be determined, e.g., by analysis of the extracted electrocardiac signal.

While the embodiments below are described with a particular emphasis to physiological condition which is a heart rate, it is to be understood that more detailed reference to the heart rate is not to be interpreted as limiting the scope of the invention in any way. For example, in exemplary embodiments of the present invention the physiological condition is a ventilation rate of the subject, a repetition rate of a particular muscle unit and/or one or more characteristics of an action potential sensed electromyography.

The adaptation of the frequency band to the physiological condition can be according to any adaptation scheme known in the art. For example, one or more parameters of the frequency band (e.g., lower bound, upper bound, bandwidth, central frequency) can be a linear function of a parameter characterizing the physiological condition. Such parameter can be, for example, the number of heart beats per minute.

Figure 4A:
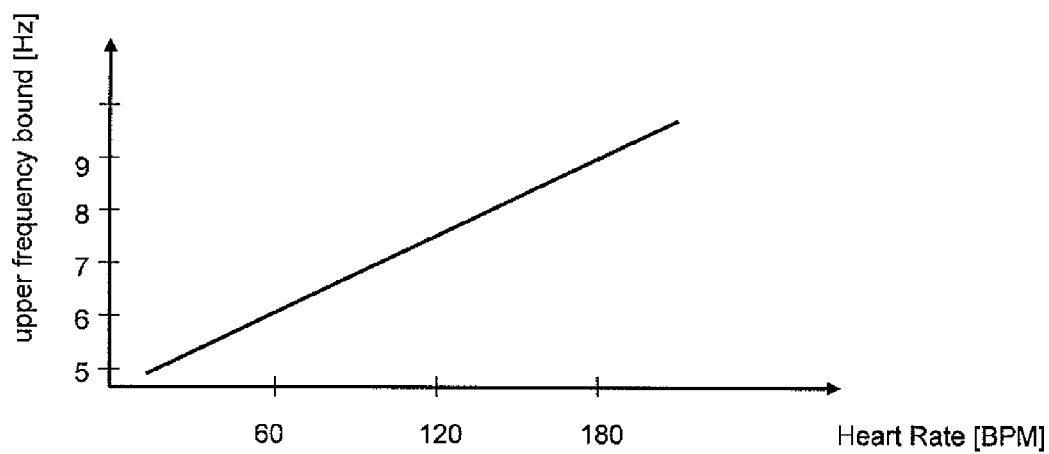
FIGS. 4a-b show a representative example of dynamically varying frequency bounds, employed according to some embodiments of the present invention.
Figure 4B:
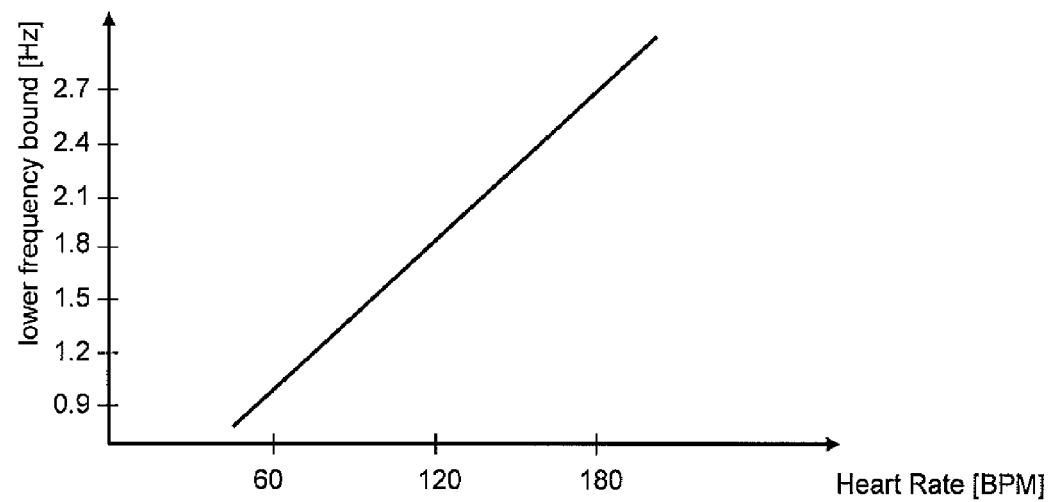

A representative example of a dynamically varying frequency bounds is illustrated in FIGS. 4a-b. Shown in FIGS. 4a-b is the functional dependence of the frequency bounds (upper bound in FIG. 4a and lower bound in FIG. 4b) on the heart rate of the subject. As shown in FIG. 4a, the upper bound of the frequency band varies linearly such that at a heart rate of about 60 beats per minute (bpm) the upper bound is about 6 Hz, and at a heart rate of about 180 bpm the upper bound is about 9 Hz. Preferably, the upper bound is about 6+1.5×[(HR/60)−1] Hz at all times, where HR is the heart rate of the subject in units of bpm. As shown in FIG. 4b, the lower bound of the frequency band varies linearly such that at a heart rate of about 60 the lower bound is about 0.9 Hz bpm and at a heart rate of about 180 bpm the lower bound is about 2.7 Hz. The lower bound is about 0.9×(HR/60) Hz at all times.

Figure 4C:
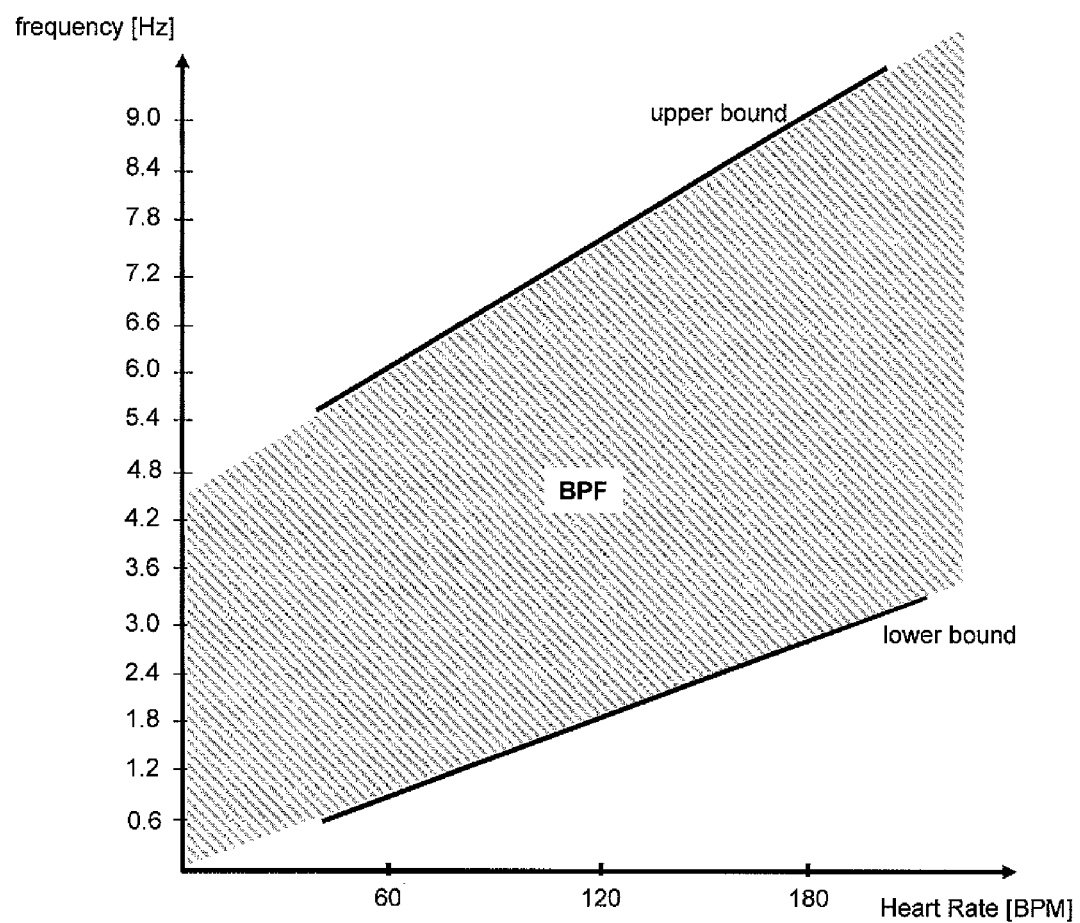
FIG. 4c show a representative example of a dynamically varying frequency band, employed according to some embodiments of the present invention.

A dynamically varying band pass filter (BPF) characterized by the frequency bounds described above is illustrated in FIG. 4c. As shown, each heart rate is associated with a frequency band defined by a lower bound and an upper bound. For example, for a heart rate of 60 bpm, FIG. 4c depicts a BPF in which the lower bound is about 0.9 Hz and the upper bound is about 6 Hz.

It is to be understood that the values presented above and the functional relations illustrated in FIGS. 4a-b are exemplary embodiments and should not be considered as limiting the scope of the present invention in any way. In other exemplary embodiments, the functional relations between the frequency band and the physiological condition can have different slopes and/or offsets, or they can be non-linear.

The procedure optionally and preferably continues to step 36 in which the cardiac output is calculated, based on $\Delta\phi$. It was found by the inventor of the present invention that there is a linear relationship between $\Delta\phi$ and the cardiac output, with a proportion coefficient comprising the systolic ejection time, T. For example, the cardiac output CO can be calculated using the relation CO=const.×T×$\Delta\phi$×HR, where HR is the heart rate of the subject (e.g., in units of beats per minutes), and "const." is a constant which can be found, for example, using a calibration curve. Step 36 can also be modified such that the stroke volume is calculated instead of the cardiac output. In this embodiment the stroke volume SV can be calculated using the relation SV=const.×T×$\Delta\phi$.

The calculated cardiac output can be used as a blood flow measure for predicting EMD onset as described above. In various exemplary embodiments of the invention the procedure continues to step 38 in which the cardiac index of the subject is calculated by dividing the cardiac output by the estimated body surface area of the subject.

Figure 5:
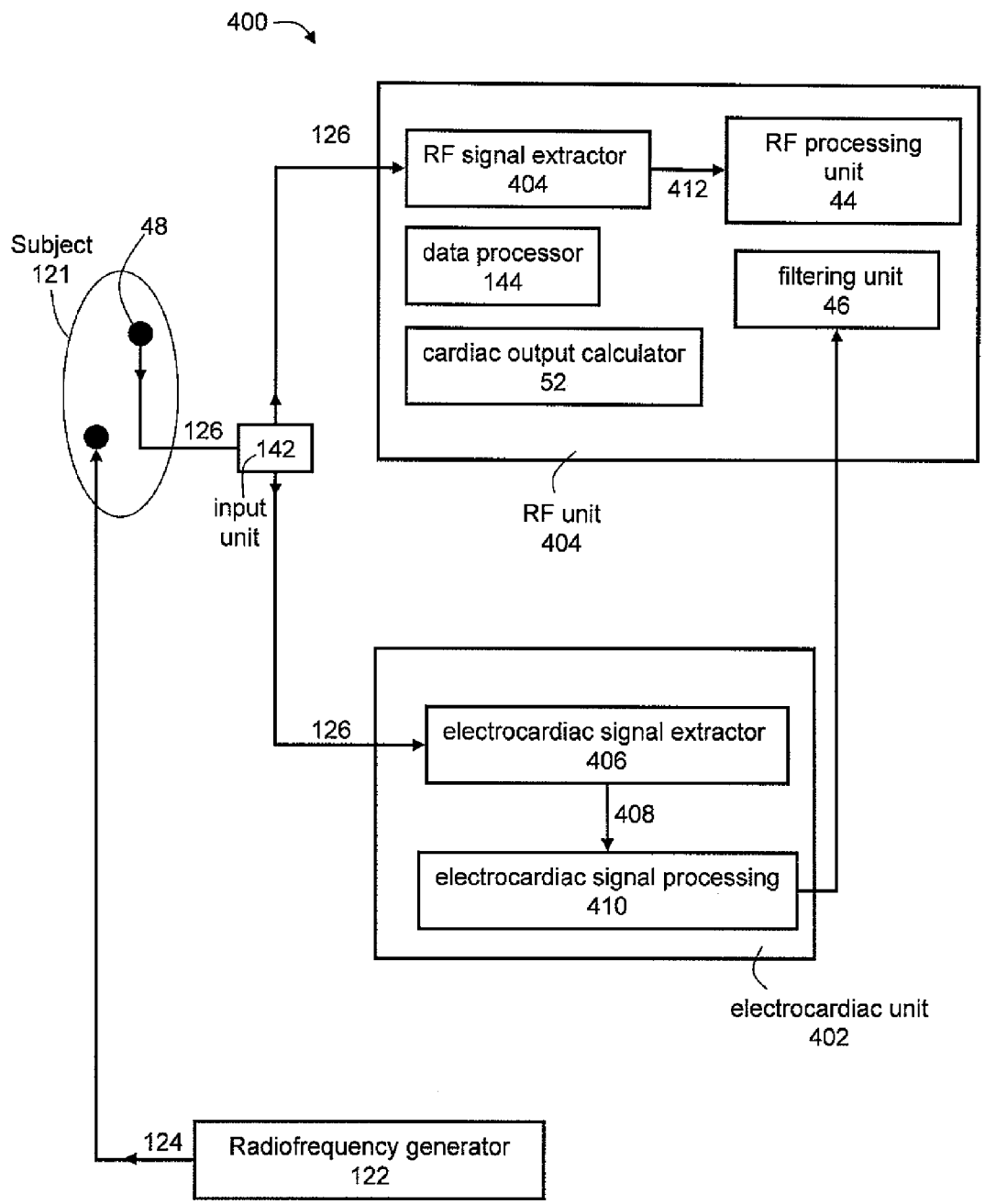
FIG. 5 is a schematic illustration of apparatus for predicting onset of electromechanical dissociation in a heart of a subject, according to various exemplary embodiments of the present invention.

Reference is now made to FIG. 5 which is a schematic illustration of apparatus 400 for predicting onset of electromechanical dissociation in a heart of a subject 121, according to various exemplary embodiments of the present invention.

Apparatus 400 generally comprises an input unit 142, an electrocardiac unit 402 and a radiofrequency unit 404.

Input unit 142 receives a composite input signal 126 from the subject. Electrocardiac unit 402 preferably comprises an electrocardiac signal extractor, which extracts an electrocardiac signal 408 from composite signal 126, and an electrocardiac signal processing unit 410 which processes signal 408 and determines the electrical activity of the heart based on signal 408. Radiofrequency unit 404 preferably comprises an RF signal extractor, which extracts an RF signal 412 from composite signal 126, and an RF signal processing unit 44 which processes signal 412.

The extracted radiofrequency signal 412 typically comprises radiofrequency signals related to the electrical properties of the organ (e.g., bioimpedance which may generally relate to the impedance and/or hemodynamic reactance of the organ). The composite signal 126 is sensed from one or more sensing locations 48 on the organ of subject 121 and is originated by output radiofrequency signals 124 generated by a radiofrequency generator 122, and action potentials originated from the sinoatrial node of the heart (not shown).

The processing of RF signal 124 may include, for example, mixing, demodulation, determination of phase shift, analog filtering, sampling and any combination thereof. Signal processing unit 44 may or may not be in communication with radiofrequency generator 122, as desired. A representative example of signal processing unit 44 is provided hereinunder with reference to FIG. 6.

Apparatus 400 is optionally and preferably designed for determining a phase shift $\Delta\phi$ of the extracted RF signal 412 relative to the generated RF signal 124. This can be done using a phase shift determinator 50 (not shown, see FIG. 6) which can operate according to any known technique for determining a phase shift. The phase shift can be determined for any frequency component of the spectrum of the extracted radiofrequency signal. For example, in one embodiment, the phase shift is determined from the base frequency component, in another embodiment the phase shift is determined from the second frequency component, and so on. Alternatively the phase shift can be determined using several frequency components, e.g., using an appropriate averaging algorithm.

The extracted radiofrequency signals may include one or more noise components, which may be introduced into the signal due to various reasons, e.g., subject agitation or breathing. In various exemplary embodiments of the invention apparatus 400 is capable of reducing or eliminating these noise components. In some embodiments of the present invention apparatus 400 further comprises a filtering unit 46 which filters the processed input signals. Unit 46 preferably performs the filtration operation in the frequency domain. Thus, in various exemplary embodiments of the invention, a series of samples of the processed radiofrequency signals are transformed, e.g., by a Fast Fourier Transform (FFT), to provide a spectral decomposition of the signals in the frequency domain. The transformation to the frequency domain can be done by a data processor 144. Algorithms for performing such transformations are known to those skilled in the art of signal processing.

The obtained spectral decomposition of the signal is filtered by unit 46 which typically eliminates one or more of the frequencies in the spectrum, depending on the upper and lower frequency bounds of the filter employed by unit 46. Unit 46 preferably employs a dynamically variable filter, such as, but not limited to, the dynamically variable filer described hereinabove. Unit 46 can employ data processor 144 for eliminating the frequency components according to the dynamically variable frequency bounds.

In some embodiments of the present invention apparatus 400 comprises a cardiac output calculator 52 which calculates the cardiac output as further detailed hereinabove. Cardiac output calculator 52 can be associated with data processor 144. Data processor 144 can also be configured for calculating other quantities, e.g., cardiac index, stroke volume and/or other blood-volume related quantities.

Figure 6:
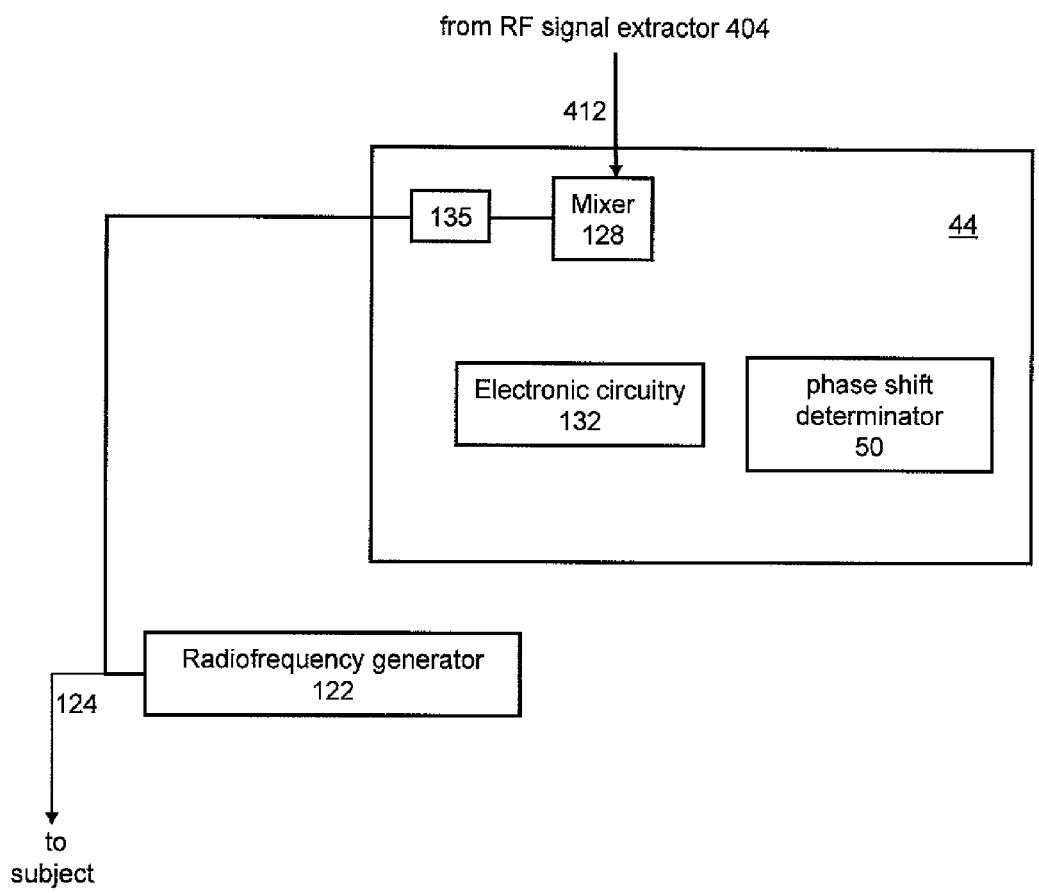
FIG. 6 is a schematic illustration of an RF processing unit, according to various exemplary embodiments of the present invention.

Reference is now made to FIG. 6 which schematically illustrates RF processing unit 44, according to various exemplary embodiments of the present invention. Unit 44 preferably comprises a mixer 128, electrically communicating with generator 122, for mixing RF signals 124 and RF signals 412, so as to provide a mixed radiofrequency signal. Signals 124 and 412 may be inputted into mixer 128 through more than one channel, depending on optional analog processing procedures (e.g., amplification) which may be performed prior to the mixing.

Mixer 128 may be any known radiofrequency mixer, such as, but not limited to, double-balanced radiofrequency mixer and unbalanced radiofrequency mixer. According to a preferred embodiment of the present invention, the mixed radiofrequency signal is composed of a plurality of radiofrequency signals, which may be, in one embodiment, a radiofrequency sum and a radiofrequency difference. A sum and a difference may be achieved, e.g., by selecting mixer 128 such that signals 124 and signals 412 are multiplied thereby. Since a multiplication between two frequencies is equivalent to a frequency sum and a frequency difference, mixer 128 outputs a signal which is composed of the desired radiofrequency sum and radiofrequency difference.

According to various exemplary embodiments of the present invention unit 44 further comprises a phase shift determinator 50 for determining the phase shift of the extracted RF signal relative to the generated output RF signal. Phase shift determinator 50 can determine the phase shift according to any technique known in the art. For example, the phase shift can be determined from the radiofrequency difference outputted from mixer 128.

According to a preferred embodiment of the present invention processing unit 44 further comprises electronic circuitry 132, which filters out a portion of the signal such that a remaining portion of the signal is characterized by a substantially increased signal-to-noise ratio.

Figure 7:
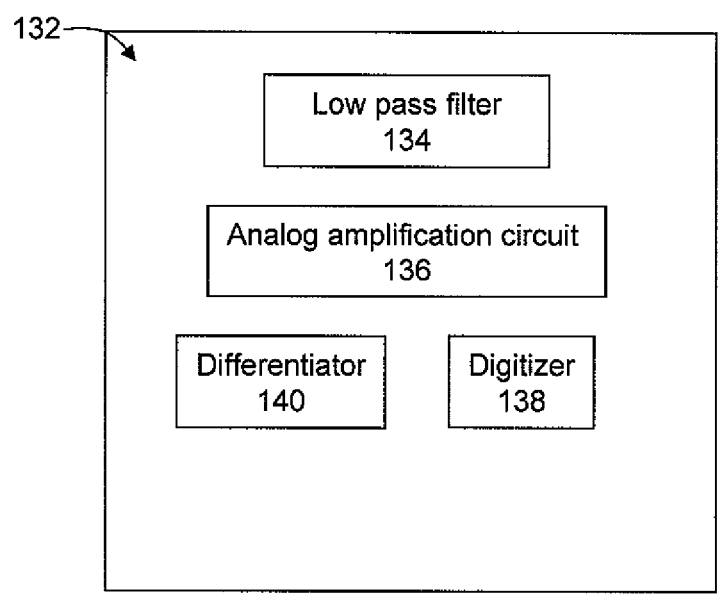
FIG. 7 is a block diagram of electronic circuitry according to various exemplary embodiments of the present invention.

Circuitry 132 is better illustrated in FIG. 7. According to an embodiment of the present invention circuitry 132 comprises a low pass filter 134 to filter out the high frequency content of the signal. Low pass filter 134 is particularly useful in the embodiment in which mixer 128 outputs a sum and a difference, in which case low pass filter 134 filters out the radiofrequency sum and leaves the approximately noise-free radiofrequency difference. Low pass filter 134 may be designed and constructed in accordance with the radiofrequency difference of a particular system which employs apparatus 400. A judicious design of filter 134 substantially reduces the noise content of the remaining portion.

Circuitry 132 preferably comprises an analog amplification circuit 136 for amplifying the remaining portion of the signal. The construction and design of analog amplification circuit 136 is not limited, provided circuit 136 is capable of amplifying the signal. Amplification circuits suitable for the present embodiments are found in International Patent Application, Publication Nos. WO 2004/098376 and WO 2006/087696 the contents of which are hereby incorporated by reference.

According to a preferred embodiment of the present invention circuitry 132 further comprises a digitizer 138 for digitizing the signal. The digitization of the signal is useful for further digital processing of the digitized signal, e.g., by a microprocessor.

Optionally, circuitry comprises a differentiator 140 (either a digital differentiator or an analog differentiator) for performing at least one time-differentiation of the measured impedance to obtain a respective derivative (e.g., a first derivative, a second derivative, etc.) of the bioimpedance or hemodynamic reactance. Differentiator 140 may comprise any known electronic functionality (e.g., a chip) that is capable of performing analog or digital differentiation.

Referring again to FIG. 6, in some embodiments of the present invention signal processing unit 44 comprises an envelope elimination unit 135 which reduces or, more preferably, eliminates amplitude modulation of signals 412. Optionally and preferably, unit 135 maintains the phase modulation of signal 412. The output of unit 135 represents the phase (or frequency) modulation of signal 412, as further detailed hereinabove. Unit 135 can employ, for example, a limiter amplifier which amplifies signals 412 and limits their amplitude such that the amplitude modulation is removed. The advantage of the removal of the amplitude modulation is that it allows a better determination of the phase shift $\Delta\phi$ between the generated and extracted RF signals, as further detailed hereinabove.

Figure 8:
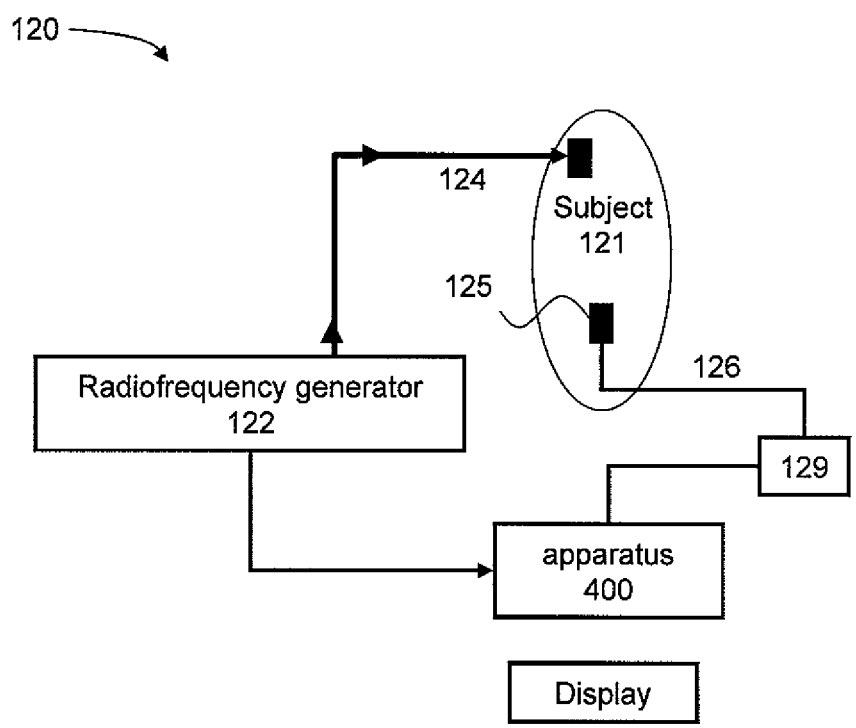
FIG. 8 is a schematic illustration of a system for predicting onset of electromechanical dissociation in a heart of a subject, according to a preferred embodiment of the present invention.

Reference is now made to FIG. 8, which is a schematic illustration of system 120 for predicting onset of electromechanical dissociation in a heart of a subject, according to a preferred embodiment of the present invention. System 120 preferably comprises a radiofrequency generator 122, for generating output radiofrequency signals. Generator 122 may be embodied as any device capable of generating radiofrequency signals. System 120 further comprises a plurality of electrodes 125, which are connected to the skin of subject 121. Electrodes 125 transmit output radiofrequency signal 124, generated by generator 122 and sense composite signal 126 which includes both the RF signal resulting from the flow of RF current across the thorax and the electrocardiac signal resulting from action potentials of the sinoatrial node.

System 120 preferably comprises any of the components of apparatus 400 described above. According to a preferred embodiment of the present invention system 120 further comprises a detector 129 for detecting a voltage drop on a portion of the body of subject 121 defined by the positions of electrodes 125. In response to the detected voltage, detector 129 preferably generates signals which are indicative of impedance or reactance of the respective portion of the body. In this embodiment, the stroke volume can be calculated using $(dX/dt)_{max}$, as further detailed hereinabove. Knowing the stroke volume, the cardiac output is calculated by multiplying the stroke volume by the heart rate of the subject. More preferably, detector 129 generates signals which are indicative of a hemodynamic reactance, X. A portion of signal 126 can also be inputted directly to the input unit of apparatus 400, e.g., for the purpose of extracting the electrocardiac signal.

Following are technical preferred values which may be used for selective steps and parts of the embodiments described above.

The output radiofrequency signals are preferably from about 10 KHz to about 200 KHz in frequency and from about 10 mV to about 200 mV in magnitude; the extracted radiofrequency signals are preferably about 75 KHz in frequency and about 20 mV in magnitude; a typical impedance which can be measured by the present embodiments is from about 5 Ohms to about 75 Ohms; the resulting signal-to-noise ratio of the present embodiments is at least 40 dB; low pass filter 134 is preferably characterized by a cutoff frequency of about 35 Hz and digitizer 138 preferably samples the signals at a rate of about 500-1000 samples per second.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of predicting onset of electromechanical dissociation in a heart of a subject using a composite input electrical signal received from the subject, the method comprising:

extracting from the composite input signal an electrocardiac signal and determining electrical activity of the heart based on said electrocardiac signal;

extracting from the composite input signal a radiofrequency signal and determining blood flow measure based on said radiofrequency signal; and if said blood flow measure is below a predetermined threshold and said electrical activity is above a predetermined threshold, then predicting a future onset of electromechanical dissociation.

2. A method of predicting onset of electromechanical dissociation in a heart of a subject, comprising:

transmitting output radiofrequency signals to the subject;
   receiving a composite input electrical signal from the subject; and
   executing the method of claim 1.

3. The method of claim 1, further comprising reducing or eliminating amplitude modulation of said radiofrequency component so as to provide a signal of substantially constant envelope.

4. The method of claim 1, further comprising filtering said radiofrequency signal using a dynamically variable filter.

5. Apparatus for predicting onset of electromechanical dissociation in a heart of a subject, the apparatus comprising:

an input unit for receiving a composite input electrical signal from the subject;
   an electrocardiac unit for extracting from the composite input signal an electrocardiac signal and determining electrical activity of the heart based on said electrocardiac signal;
   a radiofrequency unit for extracting a radiofrequency signal from the composite input signal and determining blood flow measure based on said radiofrequency signal; and
   an output unit for outputting a signal predicting a future onset of electromechanical dissociation if said blood flow measure is below a predetermined threshold and said electrical and activity is above a predetermined threshold.

6. A system for predicting onset of electromechanical dissociation in a heart of a subject, comprising:

a radiofrequency generator for generating output radiofrequency signals;
   a plurality of electrodes designed for transmitting said output radiofrequency signals to the subject and for sensing a composite input electrical signal from the subject; and
   the apparatus of claim 5.

7. The apparatus claim 5, wherein the apparatus further comprises an envelope elimination unit designed and configured for reducing or eliminating amplitude modulation of said radiofrequency signal so as to provide a radiofrequency signal of substantially constant envelope.

8. The apparatus of claim 5, wherein the apparatus further comprises a filtering unit configured for filtering said radiofrequency signal using dynamically variable filter.

9. The method of claim 4, wherein said dynamically variable filter is adapted in response to a change in a physiological condition of the subject.

10. The method of claim 9, wherein said physiological condition is a heart rate of the subject.

11. The method of claim 10, wherein a lower frequency bound characterizing said filter is about $0.9*(HR/60)$ Hz at all times, wherein said HR is said heart rate in units of beats per minute.

12. The method of claim 10, wherein an upper frequency bound characterizing said filter is about $6+1.5*[(HR/60)-1]$ Hz at all times, wherein said HR is said heart rate in units of beats per minute.

13. The method of claim 1, wherein said electrocardiac signal comprises an ECG signal.

14. The method of claim 13, wherein said determination of said electrical activity comprises determination of a QRS rate from said ECG signal.

15. The method of claim 1, wherein said blood flow measure comprises cardiac output.

16. The method of claim 15, wherein the onset of electromechanical dissociation is predicted if said cardiac output is reduced by at least 50% and said electrical activity is characterized by pulse rate of at least 60 pulses per minute.

17. The method of claim 15, wherein the onset of electromechanical dissociation is predicted if, over a period of about five minutes, said cardiac output is less than 1 liter per minute and said electrical activity is characterized by a rhythm of at least 40 cycles per minute.

18. The method claim 1, wherein said blood flow measure comprises cardiac index.

19. The method of claim 18, wherein the onset of electromechanical dissociation is predicted if, over a period of about five minutes, said cardiac index is less than 1 liter per minute per square meter and said electrical activity is characterized by a rhythm of at least 40 cycles per minute.

20. The method of claim 18, wherein the onset of electromechanical dissociation is predicted if, over a period of about five minutes, said cardiac index is less than 0.75 liter per minute per square meter and said electrical activity is characterized by a rhythm of at least 40 cycles per minute.

\* \* \* \* \*